United States Patent
Badylak et al.

(10) Patent No.: US 9,480,776 B2
(45) Date of Patent: *Nov. 1, 2016

(54) EXTRACELLULAR MATRIX BASED GASTROESOPHAGEAL JUNCTION REINFORCEMENT DEVICE

(71) Applicant: University of Pittsburgh—Of the Commonwealth System of Higher Education, Pittsburgh, PA (US)

(72) Inventors: Stephen F. Badylak, Pittsburgh, PA (US); Thomas W. Gilbert, Pittsburgh, PA (US); Alejandro Nieponice, Buenos Aires (AR)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 38 days.

This patent is subject to a terminal disclaimer.

(21) Appl. No.: 14/564,624

(22) Filed: Dec. 9, 2014

(65) Prior Publication Data

US 2015/0182663 A1 Jul. 2, 2015

Related U.S. Application Data

(63) Continuation of application No. 13/108,074, filed on May 16, 2011, now Pat. No. 8,927,003, which is a continuation of application No. 11/650,015, filed on Jan. 5, 2007, now abandoned.

(60) Provisional application No. 60/757,086, filed on Jan. 6, 2006.

(51) Int. Cl.
*A61L 27/36* (2006.01)
*A61L 27/38* (2006.01)
(Continued)

(52) U.S. Cl.
CPC ............. *A61L 27/3679* (2013.01); *A61F 2/04* (2013.01); *A61K 35/38* (2013.01); *A61L 27/362* (2013.01); *A61L 27/3629* (2013.01); *A61L 27/3633* (2013.01); *A61L 27/3882* (2013.01); *A61F 2002/044* (2013.01); *A61L 2430/22* (2013.01)

(58) Field of Classification Search
None
See application file for complete search history.

(56) References Cited

U.S. PATENT DOCUMENTS

| 3,155,095 A | 11/1964 | Brown |
| 4,902,508 A | 2/1990 | Badylak et al. |

(Continued)

OTHER PUBLICATIONS

Badylak et al., Esophageal reconstruction with ECM and muscle tissue in a dog model. J Surg Res, Sep. 2005, pp. 87-97, vol. 128, issue 1.

(Continued)

*Primary Examiner* — Allison Fox
(74) *Attorney, Agent, or Firm* — The Webb Law Firm (57) ABSTRACT

Provided are medical devices for implantation in patients having suffered the loss of or damage to at least part of their esophagus. The medical device connects the esophagus or remaining part thereof with the stomach to form a gastroesophageal junction that promotes healing and encourages new host tissue growth while distributing the load and decreasing tension at the anastomotic site. The medical device comprises extracellular matrix shaped into a conformation that more closely approximates the geometry of the native gastro-esophageal junction than does direct attachment of the stomach to the shortened esophagus. Molds useful in manufacturing the medical device and methods of use of the device are also described herein.

21 Claims, 4 Drawing Sheets

(51) Int. Cl.
A61F 2/04 (2013.01)
A61K 35/38 (2015.01)

(56) References Cited

U.S. PATENT DOCUMENTS

| | | | |
|---|---|---|---|
| 4,956,178 | A | 9/1990 | Badylak et al. |
| 5,281,422 | A | 1/1994 | Badylak et al. |
| 5,352,463 | A | 10/1994 | Badylak et al. |
| 5,372,821 | A | 12/1994 | Badylak et al. |
| 5,554,389 | A | 9/1996 | Badylak et al. |
| 5,573,784 | A | 11/1996 | Badylak et al. |
| 5,645,860 | A | 7/1997 | Knapp, Jr. et al. |
| 5,711,969 | A | 1/1998 | Patel et al. |
| 5,753,267 | A | 5/1998 | Badylak et al. |
| 5,762,966 | A | 6/1998 | Knapp, Jr. et al. |
| 5,866,414 | A | 2/1999 | Badylak et al. |
| 5,885,619 | A | 3/1999 | Patel et al. |
| 5,955,110 | A | 9/1999 | Patel et al. |
| 5,968,096 | A | 10/1999 | Whitson et al. |
| 6,099,567 | A | 8/2000 | Badylak et al. |
| 6,187,039 | B1 | 2/2001 | Hiles et al. |
| 6,241,774 | B1 | 6/2001 | Shimizu |
| 6,485,723 | B1 | 11/2002 | Badylak et al. |
| 6,576,265 | B1 | 6/2003 | Spievack |
| 6,579,538 | B1 | 6/2003 | Spievack |
| 6,696,270 | B2 | 2/2004 | Badylak et al. |
| 6,783,776 | B2 | 8/2004 | Spievack |
| 6,793,939 | B2 | 9/2004 | Badylak |
| 6,849,273 | B2 | 2/2005 | Spievack |
| 6,852,339 | B2 | 2/2005 | Spievack |
| 6,861,074 | B2 | 3/2005 | Spievack |
| 6,887,495 | B2 | 5/2005 | Spievack |
| 6,890,562 | B2 | 5/2005 | Spievack |
| 6,890,563 | B2 | 5/2005 | Spievack |
| 6,890,564 | B2 | 5/2005 | Spievack |
| 6,893,666 | B2 | 5/2005 | Spievack |
| 8,927,003 | B2 * | 1/2015 | Badylak .......... A61K 35/38 424/423 |
| 2008/0109058 | A1 | 5/2008 | Greenberg et al. |
| 2010/0023132 | A1 | 1/2010 | Imran |
| 2012/0116528 | A1 | 5/2012 | Nguyen |

OTHER PUBLICATIONS

Badylak et al., Resorbable bioscaffold for esophageal repair in a dog model, J Pediatr Surg, Jul. 2000, pp. 1097-1103, vol. 35, issue 7.
De La Fuente et al, Evaluation of porcine-derived small intestine submucosa as a biodegradable graft for gastrointestinal healing, J Gastrointest Surg, Jan. 2003, pp. 96-101, vol. 7, issue 1.
Demeester et al., The diagnosis and management of Barrett's esophagus, Adv Surg, 1999, pp. 29-68, vol. 33.
Doede et al., Unsuccessful alloplastic esophageal replacement with porcine small intestinal submucosa, Artificial Organs, 2009, pp. 328-333, vol. 33, No. 4.
Esophageal pH Monitoring, http://www.ncbi.nlm.nih.gov/pubmedhealth/PMH0003879/, Nov. 11, 2010.
Gastroesophageal Reflux Disease, http://www.ncbi,nlm.nih.gov/pubmedhealth/PMH0001311, Dec. 10, 2010.
Greenberg et al., U.S. Appl. No. 60/686,656, filed Jun. 1, 2005 (24 pages).
Heitmiller et al., Cervical Esophagogastric anastomosis: results following esophagectomy for carcinoma. Dis. Esophagus, 1999, pp. 264-269, vol. 12, issue 4.
Iannettoni et al., Catastrophic complications of the cervical esophagogastric anastomosis, J Thorac Cardiovasc Surg, Nov. 1995, pp. 1493-1500, vol. 110, issue 5.
Jobe et al., Endoscopic appraisal of the gastroesophageal value after antireflux surgery, Am J Gastroenterology, Feb. 2004, pp. 233-243, vol. 99, issue 2.
Orringer et al., Cervical esophagogastric anastomosis for benign disease. Functional results, J. Thorac Cardiovasc Surg, Dec. 1988, pp. 887-893, vol. 96, issue 6.
Orringer et al., Transhiatal esophagectomy for treatment of benign and malignant esophageal disease, World J Surg, Feb. 2001, pp. 196-203, vol. 25, issue 2.
Reavis et al., Utilization of the Delay Phenomenon Improves Blood Flow, Ann Surg, May 2005, pp. 736-747, vol. 241, issue 5.
Richter et al., Normal 24-Hr ambulatory esophageal pH values: Influence of study center pH electrode, age, and gender, Dig. Dis. and Sci, Jun. 1992, pp. 849-856, vol. 37, issue 6.
Rizk et al., The impact of complications on outcomes after resection for esophageal and gastroesophageal junction carcinoma, J Am Coll Surg, Jan. 2004, pp. 42-50, vol. 198, issue 1.
Santucci et al., Resorbable extracellular matrix grafts in urologic reconstruction, Int Braz J Urol, May-Jun. 2005.
Sato et al., Material Science Forum, 1997, vol. 250, pp. 105-114.
Schuchert et al., Impact of anastomotic leak on outcomes after transhiatal esophagectomy, Surgery, Oct. 2010, pp. 831-838, vol. 148, issue.
Stein et al., Limited resection for early adenocarcinoma in Barrett's esophagus, Ann Surg, Dec. 2000, pp. 733-742, vol. 232, issue 6.
Venere, New materials hold promise for human healing applications, Purdue News, Mar. 22, 2001.
Whyte et al., Surgery for Carcinoma of the Esophagus: The Case for Transhiatal Esophagectomy. Semin Radiat Oncol, Jul. 1994, pp. 146-156, vol. 4, issue 3.
Wright Medical Technology, Comparative analysis: GRAFTJACKET TM Periosteum Replacement Scaffold & SIS TM Porcine Small Intestine Submucosa, 2002.
Yildirim et al., Colonic interposition vs. gastric pull-up after total esophagectomy, J Gastrointest Surg, Sep.-Oct. 2004, pp. 675-678, vol. 8, issue 6.

* cited by examiner

FIG. 4B

EXTRACELLULAR MATRIX BASED GASTROESOPHAGEAL JUNCTION REINFORCEMENT DEVICE

CROSS REFERENCE TO RELATED APPLICATIONS

This application is a continuation of U.S. patent application Ser. No. 13/108,074, filed May 16, 2011, now U.S. Pat. No. 8,927,003, which is a continuation of U.S. patent application Ser. No. 11/650,015, filed Jan. 5, 2007, now abandoned, which claims the benefit of U.S. Provisional Patent Application No. 60/757,086, filed on Jan. 6, 2006, each of which is incorporated herein by reference in its entirety.

Described herein are medical devices for implantation in patients that may be used to connect an esophagus or portions thereof with a stomach to form and/or repair a gastro-esophageal junction. Methods of use of the medical device are also described herein.

Surgical procedures involving the esophagus have always been challenged by their high morbidity and mortality rates (Orringer and Stirling, 1988, J Thorac Cardiovasc Surg. 96:887-93; Heitmiller et al., 1999, Dis Esophagus. 12:264-9; Whyte and Orringer, 1994, Semin Radiat Oncol. 4:146-156). Radical esophagectomy, the therapy of choice for patients with esophageal cancer or patients with high grade dysplasia, is usually followed by a complex reconstructive surgery to restore food transit. The most commonly accepted approach has been mobilizing the stomach through the mediastinum after shaping it into a tube and anastomosing it to the remaining cervical esophagus ("gastric pull-up") (Orringer et al., 2001, World J Surg. 25:196-203). When the stomach is not available, other options such as colonic or small bowel interposition are utilized (Yildirim, 2004, J Gastrointest Surg. 8:675-8). Although partially successful, the outcome of these procedures remains suboptimal due to the high associated morbidity (Iannettoni et al., 1995, J Thorac Cardiovasc Surg. 110:1493-500). The mobilization of the abdominal organs into the mediastinal cavity usually yields to extensive compromise of the blood supply and the resulting poorly vascularized tissue has a reduced healing capacity that contributes to complications at the anastomotic site (Reavis et al., 2005, Ann Surg. 241:736-45). Anastomotic leakage is the most common complication associated with high morbidity and it is considered an independent risk factor in the prognostic outcome (Rizk et al., 2004, J Am Coll Surg. 198:42-50). For many years, surgeons have attempted modifications of the surgical technique to improve this condition with limited success. In fact, controversy still exists on whether a complete mechanical anastomosis significantly decreases the leak rate when compared to a hand sewn anastomosis. Another common complication related to poor healing capacity and scarring is the post-operative stricture of the anastomosis that requires endoscopic dilation in up to 50% of patients (Orringer et al., 2001, World J Surg. 25:196-203). On the other hand, partial resection of the esophagus (i.e. mucosectomy in Barret's disease) is limited by the inability of the tissue to regenerate in an organized manner and leads to scar tissue formation and ultimately esophageal stenosis (Stein et al., 2000, Ann Surg. 232:733-42; DeMeester and DeMeester, 1999, Adv Surg. 33:29-68).

There exists a need for anastomotic reinforcement in connection with surgical procedures involving the esophagus. Recently, regenerative medicine approaches have shown promising results using extracellular matrix (ECM) scaffolds derived from the small intestinal submucosa (SIS) and urinary bladder (UBM) in the attempt to reconstitute normal tissue. Several pre-clinical and clinical applications have been reported for numerous body structures including vascular, skin, musculo-skeletal, lower urinary tract, and esophageal tissue.

STATEMENT REGARDING FEDERAL FUNDING

This invention was made with government support under Grant No. 1 R43 DK069110-01, awarded by the National Institutes of Health. The government has certain rights in this invention.

SUMMARY

ECM scaffolds are provided as anastomotic reinforcement devices and to reduce scarring and inflammation to better promote healing with decreased complications. Thus provided, according to one embodiment of the medical devices described herein, are medical devices for implantation in patients having lost at least part of their esophagus or having damage to their esophagus. According to one embodiment, the medical devices described herein connect the esophagus or remaining part of the esophagus with the stomach to form a gastro-esophageal junction that promotes healing and encourages new host tissue growth, diminishes scar tissue formation and stricture while distributing the load, decreasing tension, and increasing vascular perfusion at the anastomotic site. The medical device comprises extracellular matrix (ECM) shaped into a conformation that more closely approximates the geometry of the native gastro-esophageal junction than does direct attachment of the remaining stomach, often tubularized, to the shortened esophagus. Methods of use of the medical device are also encompassed by the present invention.

In one embodiment, a device is provided comprising one or more layers of extracellular matrix tissue, for example and without limitation 2-10 layers, and comprising a tubular esophageal portion having essentially a constant diameter (the diameter can increase, decrease or vary so long as it substantially conforms with a shape of a portion of an esophagus); and a tubular gastric portion attached to the esophageal portion at a junction having a diameter that increases from the junction to a distal tip of the gastric portion. The diameter of the gastric portion may increases in an essentially uniform manner from the junction to the distal tip of the gastric portion. Typically, the gastric portion is modeled to conform with a portion of a patient's stomach to which a remaining portion of the patient's esophagus is to be attached, and in one embodiment, the gastric portion is modeled to conform with a cardiac region of a stomach adjacent to a cardiac opening of the stomach.

In certain embodiments, the esophageal portion has a length of between 1 to 30 cm and a diameter of between 0.5 to 5 cm; and/or the gastric portion has a length of between 1 to 8 cm and the distal tip of the gastric portion has a diameter of between 1-12 cm. According to other embodiments, the esophageal portion has a length of about 3 cm and a diameter of about 2.3 cm; and/or the gastric portion has a length of about 3-4 cm and a diameter of the distal tip of about 7 cm.

The extracellular matrix tissue may be isolated by any useful method from any useful source. In one example, the tissue is isolated from urinary bladder tissue, for example and without limitation porcine urinary bladder tissue. The extracellular matrix tissue may comprise epithelial basement membrane and subjacent tunica propria. The extracellular matrix tissue may comprise tunica submucosa. The extracellular matrix tissue may comprise epithelial basement membrane, subjacent tunica propria, tunica submucosa and/or tunic muscularis. The extracellular matrix tissue also may be isolated from intestinal submucosa, esophagus or dermis of skin. The device may be seeded with cells, typically human cells, such as a patient's cells into whom the device is to be implanted or allogeneic cells. The cells may be implanted in the device prior to surgery and may be allowed to populate the device prior to surgery by incubation in a bioreactor. Alternately, autologous or allogeneic cells may be implanted at the time of surgery, for example and without limitation, by attaching a suitable piece of tissue to the device during implantation surgery.

Also provided is a mold for molding extracellular matrix tissue into a device as described herein, comprising a tubular esophageal portion having essentially a constant diameter (the diameter can increase, decrease or vary so long as it substantially conforms with a shape of a portion of an esophagus), and a tubular gastric portion attached to the esophageal portion at a junction, the gastric portion having a diameter that increases from the junction to a distal tip of the gastric portion. As with the device described herein, the diameter of the gastric portion of the mold may increase in an essentially uniform manner from the point of connection to the esophageal portion to the distal tip of the gastric portion. In other embodiments, the esophageal portion of the mold has a length of between 1 to 30 cm and a diameter of between 0.5 to 5 cm; and the gastric portion has a length of between 1 to 8 cm and the distal tip of the gastric portion has a diameter of between 1-12 cm. In further embodiments, the esophageal portion has a length of about 3 cm and a diameter of about 2.3 cm; and the gastric portion has a length of about 3-4 cm and a diameter of the distal tip of about 7 cm. The mold may be made of one or more water-permeable materials. In certain embodiments, the gastric portion is modeled to conform with a portion of a stomach, for example and without limitation, the gastric portion is modeled to conform with a cardiac region of a stomach adjacent to a cardiac opening of the stomach. Due to variations in esophageal and gastric geometry prior to and after surgery, the esophageal portion of the mold may be detachable from the gastric portion to allow interchangeability of different-shaped gastric portions. Further, the mold may be collapsible by any means known in the art to facilitate removal of the device from the mold.

In another embodiment of the technology described herein, a method is provided of reinforcing an anastomotic site in a patient comprising implanting a device between a portion of (e.g., that portion remaining after surgery) the patient's esophagus and stomach, the device can be any device comprising one or more layers of extracellular matrix tissue and comprising a tubular esophageal portion having essentially a constant diameter; and a tubular gastric portion attached to the esophageal portion at a junction having a diameter that increases from the junction to a distal tip of the gastric portion and variations thereof described herein. In certain embodiments, the patient has or previously has had Barrett's disease, esophageal cancer, congenital atresia, or trauma to the esophagus.

BRIEF DESCRIPTION OF THE DRAWINGS

FIG. 2A provides two views of a first embodiment and FIG. 2C provides a single view of a second embodiment as described herein. The esophageal and gastric portions of the device are indicated as well as the proximal and distal tips of the device.

DETAILED DESCRIPTION

The present invention is related to a medical device to be implanted in patients having suffered the loss of or damage to at least part of their esophagus. The device comprises one or more layers of extracellular matrix (ECM) molded into a particular shape that more closely approximates the geometry of the native gastro-esophageal junction than does direct attachment of the remaining stomach to the shortened esophagus. In one embodiment, the ECM is molded into a shape that essentially recapitulates the native geometry of the gastro-esophageal junction (the portions of the stomach and esophagus adjacent to the cardiac orifice) prior to tissue loss. The device serves as an inductive support scaffold that facilitates constructive remodeling of this site following segmental esophagectomy.

As used herein, the terms "extracellular matrix" and "ECM" refer to a complex mixture of structural and functional biomolecules including, but not limited to, structural proteins, specialized proteins, proteoglycans, glycosaminoglycans, and growth factors that surround and support cells within mammalian tissues.

Any type of extracellular matrix tissue can be used to make a device as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). In certain embodiments, the ECM is isolated from a vertebrate animal, for example and without limitation, from a warm blooded mammalian vertebrate animal including, but not limited to, human, monkey, pig, cow and sheep. The ECM can be derived from any organ or tissue, including without limitation, urinary bladder, intestine, liver, esophagus and dermis. In one embodiment, the ECM is isolated from a urinary bladder. The ECM may or may not include the basement membrane portion of the ECM. In certain embodiments, the ECM includes at least a portion of the basement membrane. The material used to make the ECM Device may comprise primarily (that is, greater than 70%, 80%, or 90%) ECM. This material may or may not retain some of the cellular elements that comprised the original tissue such as capillary endothelial cells or fibrocytes.

Figure 1:
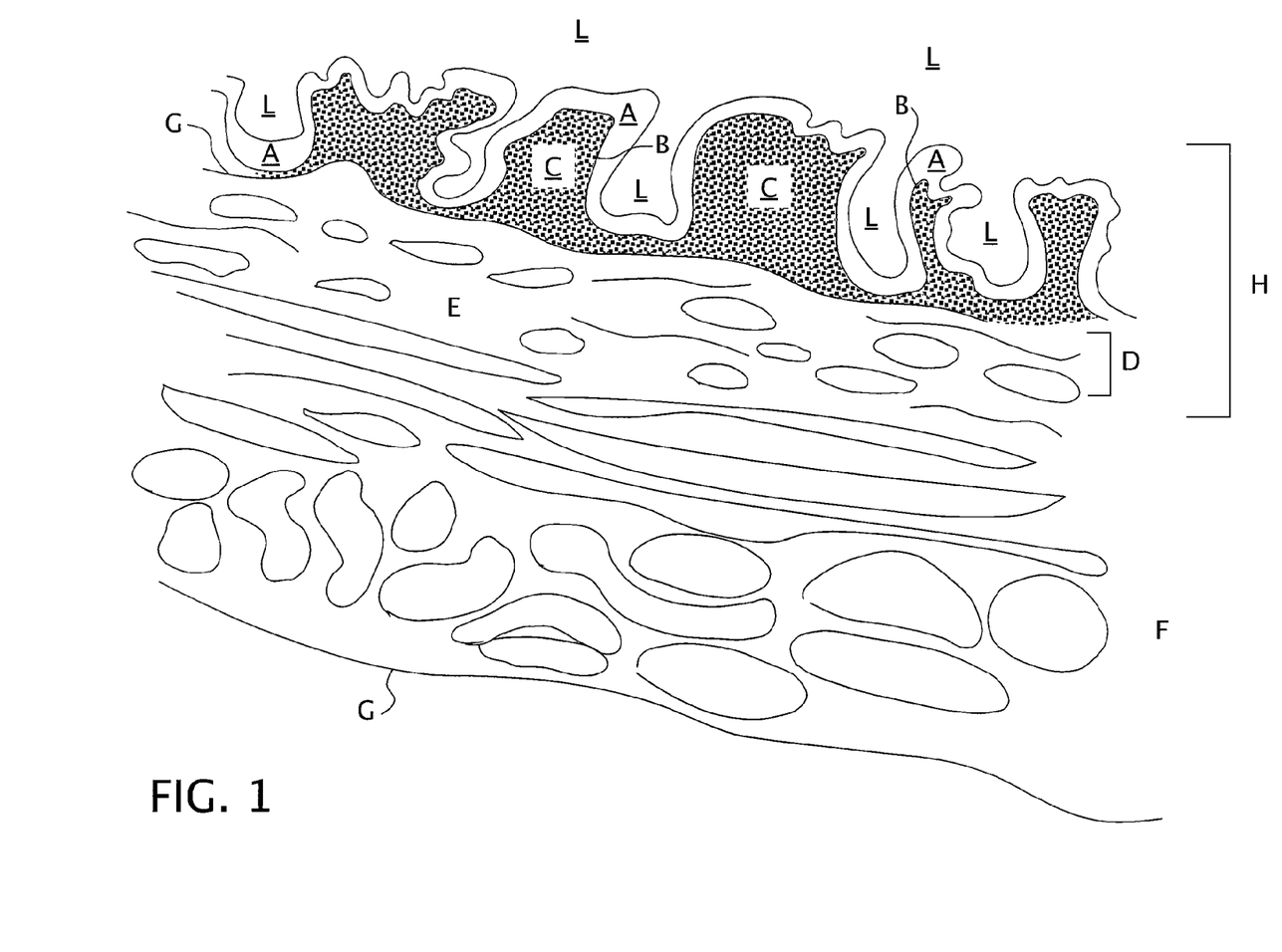
FIG. 1 is a schematic of a cross-sectional view of the wall of the urinary bladder (not drawn to scale). The following structures are shown: epithelial cell layer (A), basement membrane (B), tunica propria (C), muscularis mucosa (D), tunica submucosa (E), tunica muscularis externa (F), tunica serosa (G), tunica mucosa (H), and the lumen of the bladder (L).

In one embodiment, the ECM is harvested from porcine urinary bladders. Briefly, the ECM is prepared by removing the urinary bladder tissue from a pig and trimming residual external connective tissues, including adipose tissue. All residual urine is removed by repeated washes with tap water. The tissue is delaminated by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion. Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. After these tissues are removed, the resulting ECM consists mainly of epithelial basement membrane and subjacent tunica propria (layers B and C of FIG. 1).

In another embodiment, the ECM is prepared by abrading porcine bladder tissue to remove the outer layers including both the tunica serosa and the tunica muscularis (layers G and F in FIG. 1) using a longitudinal wiping motion with a scalpel handle and moistened gauze. Following eversion of the tissue segment, the luminal portion of the tunica mucosa (layer H in FIG. 1) is delaminated from the underlying tissue using the same wiping motion. Care is taken to prevent perforation of the submucosa (layer E of FIG. 1). After these tissues are removed, the resulting ECM consists mainly of the tunica submucosa (layer E of FIG. 1).

The ECM can be sterilized, and typically decellularized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced by physical and/or chemical methods, including without limitation, treatment with carbodiimide or dehydrothermal or photooxidation methods. More typically, ECM is disinfected by immersion in 0.1% (v/v) peracetic acid ($\sigma$), 4% (v/v) ethanol, and 96% (v/v) sterile water for 2 h. The ECM material is then washed twice for 15 min with PBS (pH=7.4) and twice for 15 min with deionized water.

Commercially available ECM preparations can also be used to make the ECM Device of the invention. In one embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another embodiment, the ECM is derived from dermis. Commercially available preparations include, but are not limited to Pelvicoff™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

In further embodiments, the device may be seeded with cells, typically autologous or allogeneic cells, prior to or during implantation. In one example, the device is co-cultured ex vivo in a suitable bioreactor with a patient's (allogeneic) cells or with cells from another patient (allogeneic). Suitable cells are, for example and without limitation, smooth muscle cells, bone marrow cells, cheek scrapings and biopsies from healthy esophageal or intestinal tissue from the patient or from another patient. Cells from a patient, such as cells obtained from a biopsy of healthy tissue obtained during surgery can be seeded onto the device, for example by suturing a small portion the other tissue onto the device during surgery. Variations on these methods would be apparent to one of skill in the art.

Figure 2A:
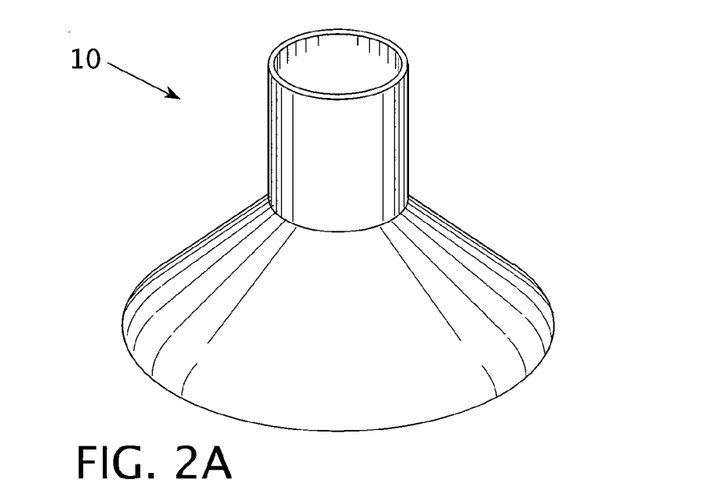
FIGS. 2A-2C show schematically two embodiments of an extracellular matrix device described herein.
Figure 2B:
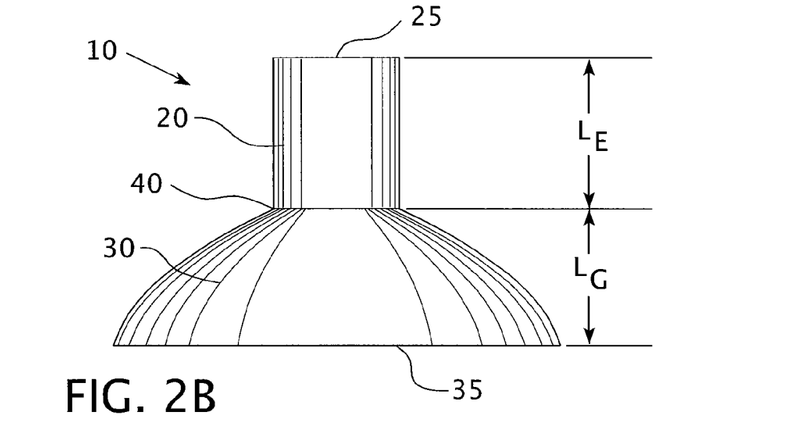
Figure 2C:
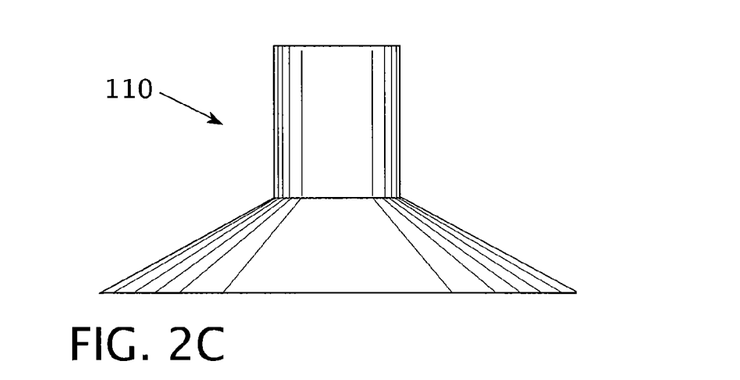

According to one embodiment of the device described herein, the ECM device is molded to closely approximate the shape of a gastro-esophageal junction, for example and without limitation, a human gastro-esophageal junction. The mold used to process the extracellular matrix (ECM) into the ECM Device of the invention can be made from any suitable material, such as, without limitation, a plastic and is shaped into a form that approximates the geometry of the native gastro-esophageal junction. This mold structure forms an ECM device that more closely approximates the shape of a native gastro-esophageal junction than the shape of the junction formed by direct attachment of the remaining stomach to the shortened esophagus during standard esophagectomy surgical procedures. In reference to the ECM device shown in FIGS. 2A and 2B, the ECM device 10, as well as its mold are generally funnel-shaped and comprise an esophageal portion 20 of length LE ending in a proximal tip 25 and a gastric portion 30 of length LG ending in a distal tip 35 (see FIG. 2). Esophageal portion 20 and gastric portion 30 are joined at junction 40. Esophageal portion 20 is tubular and has a diameter that is essentially constant. Gastric portion 30 also is tubular, but its diameter increases from the junction 40 to the distal tip 35 in a shape that is roughly frustro-conical, but which has a curved profile as the gastric portion 30 radiates from the junction 40 to the distal tip 35. In use, esophageal portion 20 of the ECM device 10 is connected to the gastric (inferior) end of the remaining esophagus in a patient to be treated while the gastric portion 30 of the ECM device 10 is connected to the stomach in the patient to be treated. FIG. 2C shows an alternate embodiment of device 110 in which the gastric portion is frustro-conical in that this embodiment exhibits a linear profile as the gastric portion radiates from the junction to the distal tip.

The mold may comprise two detachable parts, a gastric portion and an esophageal portion. The size and shape of the esophagus of many patients may vary from patient-to-patient, as would the size and shape of the stomach to which the device would be implanted. Further, the surgical procedure requiring the device would vary, with some surgeons tubularizing the portion of the stomach to which the device is attached to varying extents. As such, according to one embodiment, a number of different-sized and different-shaped gastric and esophageal mold portions are provided that can be independently matched in order to customize the ECM device. The two portions can connect by any useful method.

Figure 3A:
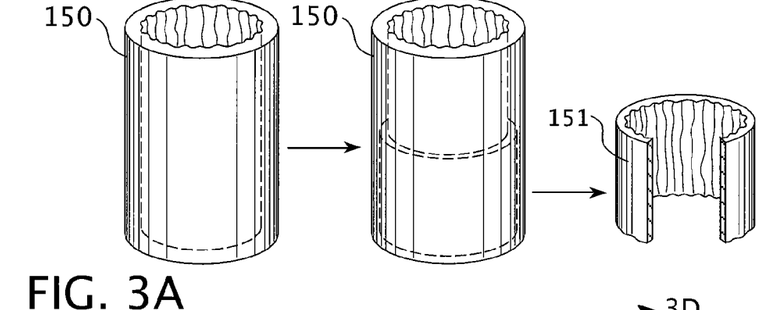
FIGS. 3A-3D schematically show implantation of one embodiment of a device described herein in a cervical esophageal anastomosis.
Figure 3B:
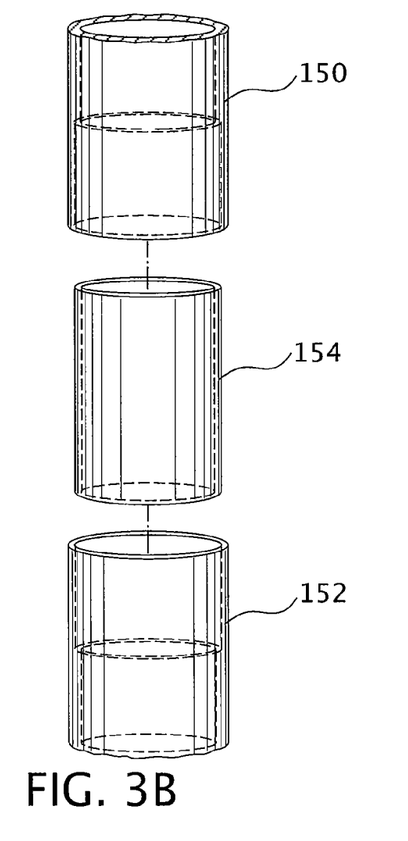
Figure 3C:
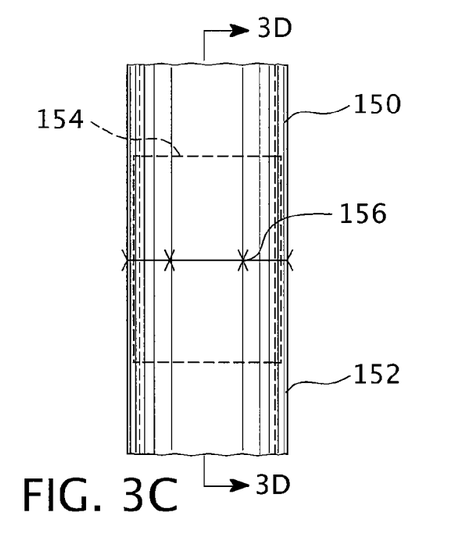
Figure 3D:
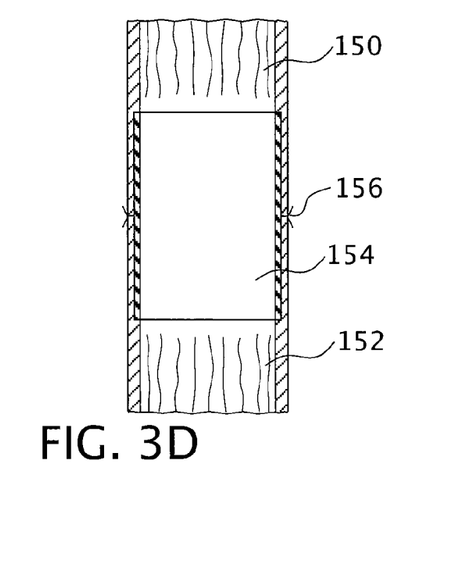

FIGS. 3A-3D schematically show a cervical esophageal anastomosis using one embodiment of a device described herein. FIG. 3A shows a superior terminus of an upper esophagus 150 to be attached to an inferior terminus of a lower portion (152 in FIGS. 3B-3D) of the same esophagus. The inner wall of superior terminus 150 is shown in phantom. In preparation for anastomosis, endomucosa 151 is removed from the end of superior terminus 150 as shown. FIG. 3B is an exploded view of the anastomosis, showing superior terminus 150, inferior terminus 152 and ECM device 154. Endomucosa is removed from inferior terminus 152 in the same manner as with superior terminus 150 shown in FIG. 3A. FIG. 3C and 3D show completed anastomosis. FIG. 3C shows an exterior view of superior terminus 150 and inferior terminus 152, sutured with sutures 156 and with ECM device 154 shown in phantom. FIG. 3D shows a cross-sectional view of the repaired esophagus shown in FIG. 3C, showing superior terminus 150, inferior terminus 152, ECM device 154 and sutures 156.

Figures 4A, 4B, 4C:
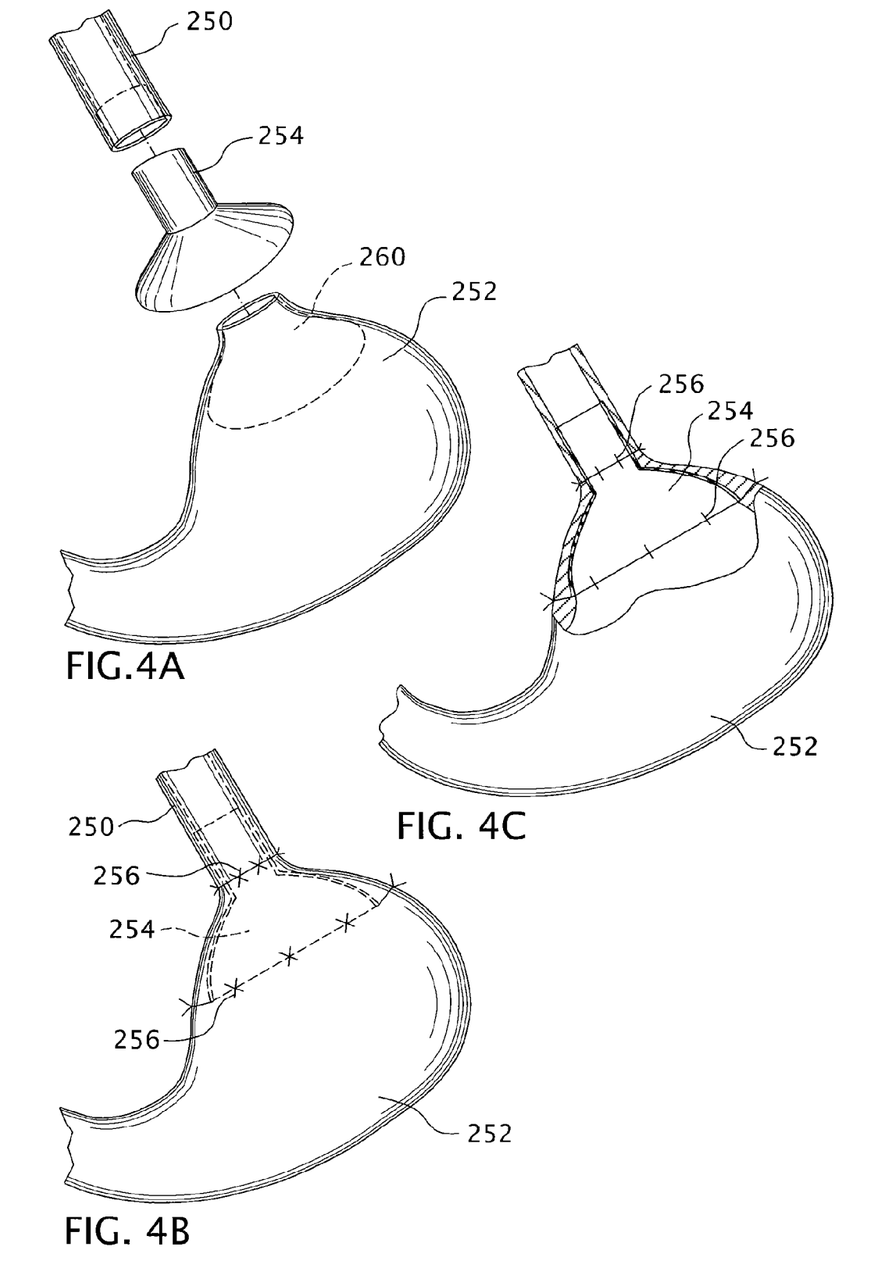
FIGS. 4A-4C show implantation of one embodiment of a device described herein in a gastro-espohageal junction anastomosis.

FIGS. 4A-4C show anastomosis of superior terminus 150 of esophagus to a stomach 252 according to one embodiment of the methods described herein. FIG. 4A is an exploded view of the anastomosis, showing superior terminus 250, stomach 252 and ECM device 254. As with FIG. 3A, endomucosa is removed from the end of superior terminus 250 and from cardiac region 260 of the stomach 252 in preparation for anastomosis. FIG. 4B and 4C show completed anastomosis. FIG. 4B shows an exterior view of superior terminus 250 and stomach 252, sutured with sutures 256 and with ECM device 254 shown in phantom. Figure 4C shows a cross-sectional view of the repaired gastro-esophageal junction shown in FIG. 4B, showing superior terminus 250, stomach 252, ECM device 254 and sutures 256.

It will be apparent to those of skill in the art that the anastomosis methods illustrated in FIGS. 3A-3D and 4A-4C are for illustration purposes only and variations in this surgical procedures would be apparent to surgeons and others of skill in the art. For instance, some surgeons would not remove the endomucosa from the esophageal and/or stomach portions. Further, the ECM device might be placed external to (on the outside of) the stomach and esophagus. In that case, the stomach and remaining esophagus is attached and then the device is sewn on the outside of the newly-formed gastro-esophageal junction. During the surgical procedure, the device may be trimmed or modified as a surgeon sees fit in order to further customize the device.

A kit also may be provided that includes suitable, typically sterile packaging and the device according to any embodiment described herein. Suitable packaging materials and configurations are known in the art. For example and without limitation, any device described herein can be distributed in a blister pack comprising a plastic container with a foil, plastic and/or paper tear-away cover. This kit would be suitable for shipping or other distribution from a manufacturing facility to an end-user or distribution point in the relevant market.

As used herein, the terms "essentially," "substantially," and "about" refer to slight variations in structure or function that approximate a stated value and slight variations in tolerances are acceptable in the usefulness of a device, apparatus or method. For example, in the context of a device described herein, the diameter of the esophageal portion may be described as "essentially constant" meaning that slight variations in diameter are tolerable, so long as the device can function in the desired context, that is, for example and without limitation, for reinforcement of esophageal or gastro-esophageal anastomosis.

The actual dimensions of the mold to be used will be largely dictated by the needs of a patient to be treated. The dimensions will vary depending on the native esophageal and stomach tissue and the particular diameter/morphology of the remaining stomach and/or esophagus. The esophageal portion of the mold typically has a length of between 1 to 30 cm. The gastric portion of the mold has a length of between 1 to 8 cm. In some embodiments, the esophageal portion and the gastric portion of the mold are approximately equal in length. In other embodiments, the esophageal portion and the gastric portion of the mold are unequal in length. In a specific embodiment, the esophageal portion of the mold is longer in length than the gastric portion of the mold. In another specific embodiment, the gastric portion of the mold is longer in length than the esophageal portion of the mold. The gastric portion typically is modeled after (molded to conform to) a portion of a patient's stomach, typically, but not exclusively to a cardiac portion of a patient's stomach (that portion of a patient's stomach immediately adjacent to the cardiac opening at the gastro-esophageal junction).

The esophageal portion of the mold is generally narrower in diameter than the gastric portion of the mold and typically has an inner diameter of between 0.5 to 5 cm.

The gastric portion of the mold does not have a constant inner diameter. Rather, the diameter increases from the point of connection to the esophageal portion to the distal tip. The increase in diameter throughout the gastric portion can be a uniform gradient or it can be a non-uniform in gradient. In one exemplary embodiment, the diameter of the gastric portion increases in a (linear or non-linear) uniform gradient from the junction between the esophageal portion and the gastric portion to the distal tip. The distal tip of the gastric portion of the mold typically has an inner diameter of between 1 to 12 cm.

The gastric portion can be any shape. The shape of the gastric portion includes, but is not limited to, conformations that result in the distal tip being circular, ellipsoid, octagonal, hexagonal, pentagonal, etc. In one embodiment, the gastric portion is shaped such that the distal tip is circular.

In one particular embodiment, the esophageal portion of the mold has an internal diameter of about 2.3 cm and a length of about 3 cm while the gastric portion has an internal diameter of the distal tip of about 7 cm and a length of about 3-4 cm.

The mold may be made of any material compatible with the processing described above. In certain embodiments, the material is water-permeable. As used herein, the term "water-permeable" includes surfaces that are water absorbent, microporous or macroporous. Macroporous materials include perforated plates or meshes made of plastic, metal, ceramics or wood. Macroporous materials, such as perforated materials or screens, are useful in the drying process because they result in increased available device surface area and they facilitate the ability to create a vacuum on the inside of the mold and therefore on an inside surface of the device, for example as described below.

As used herein, the term "Extracellular Matrix Device" refers to extracellular matrix that has been applied to a mold as described herein and processed such that it has adopted the shape of the mold (see generally U.S. Pat. Nos. 5,885,619; 5,955,110; 5,968,096; and 6,187,039).

The mold for the ECM Device may be wrapped with a protective layer to facilitate removal of the ECM from the mold after processing. In one embodiment, the mold is wrapped with umbilical tape. In another embodiment, the mold is wrapped with cheese cloth. In one particular embodiment, the esophageal portion of the mold is wrapped in umbilical tape and the gastric portion of the mold is wrapped in cheese cloth. The mold also may be collapsible to facilitate removal of the device. For example and without limitation, folding points may be incorporated into the mold, or the mold may be splittable into two or more portions.

Any number of layers of ECM can be used to make the ECM device. In one embodiment 2-20 layers of ECM are used. In another embodiment, 2-10 layers of ECM are used. In yet another embodiment, 3-6 layers of ECM are used. In a further embodiment, 4 layers of ECM are used.

One or more hydrated sheets of ECM are formed around the mold. Where the sheets of ECM overlap (either the two ends of a single ECM sheet fully wrapped around the mold or the ends of two different sheets of ECM each partially wrapped around the mold), the seam formed can be sutured to form a water tight seal and/or can be fixed to one another using standard techniques known to those skilled in the art (for example and without limitation, with a crosslinking agent such as glutaraldehyde). The mold and ECM are then placed under compression conditions including, but not limited to, placement into a plastic pouch and attachment to a vacuum pump (e.g., Leybold, Export, Pa., Model D4B) with a condensate trap inline under a vacuum of 28 to 29 in Hg for 10 to 12 h.

In one embodiment the mold and ECM are compressed under dehydrating conditions. As used herein, the term "dehydrating conditions" refers to any mechanical or environmental condition which promotes or induces the removal of water from the ECM. To promote dehydration of the compressed ECM, at least one of the surfaces compressing the tissue is water permeable. Dehydration of the tissue can optionally be further enhanced by applying blotting material, heating the tissue or blowing air across the exterior of the compressing surfaces.

After compression, the ECM Device is then removed from the mold and terminally sterilized, for example and without limitation, with ethylene oxide.

A patient having any disorder involving the loss or absence of at least a portion of the esophagus can be treated using the methods and devices described herein. In certain non-limiting embodiment, the patient to be treated by the methods and devices described herein has lost at least 10%, 25%, 35%, 50%, 75%, 80%, or 90% of the length of their esophagus. In another embodiment, the patient to be treated by the methods and devices described herein has lost the full circumference of at least part of their esophagus. In another embodiment, the patient to be treated by the methods and devices described herein has lost less than the full circumference of at least part of their esophagus including, but not limited to, at least 10%, 25%, 35%, 50%, 75%, 80%, or 90% of the circumference of the esophagus. In such an embodiment, the portion of the circumference of the esophagus missing may or may not be contiguous. In another embodiment, the patient to be treated by the methods and devices described herein has lost at least a portion of the lining of the esophagus but retains at least some autologous muscle tissue and/or submucosal layer of the esophagus.

In a specific embodiment, patients suffering from or having previously suffered from Barrett disease are treated using the ECM device of the invention.

In another specific embodiment, patients suffering from or had previously suffered from esophageal cancer are treated using the ECM device of the invention.

EXAMPLES

Overview of Experimental Design

Sixteen adult healthy mongrel dogs weighing between 17 and 24 kg were divided into 2 groups. Each dog was subjected to a complete transection of the esophagus and anastomosed in an end-to-end fashion. Both groups were reinforced with an ECM scaffold that was telescoped inside the anastomosis. The measured endpoints included esophageal function and morphological characteristics.

Group 1: Cervical Esophageal Anastomosis

The dogs in group 1 (n=6) were subjected to a complete transection of the esophagus in the mid-cervical region with surgical resection of 1.5 cm of the full circumferential endomucosa from both ends. The endomucosa was defined as the epithelium, basal lamina (basement membrane), lamina, plus the tunica submucosa, leaving only the muscularis externa. A tubularized form of the urinary bladder matrix (UBM) was anastomosed to the ends of the remaining endomucosa, and the ends of the overlying muscularis externa were anastomosed (see, e.g., FIGS. 3A-3D). A control dog underwent the same surgical procedure without device implantation.

Group 2: Gastroesophageal Junction Anastomosis

The dogs in group 2 (n=6) were subjected to a complete section of the gastroesophageal (GE) junction to assess the remodeling of the ECM in an acidic environment; the environment of an anastomosis created during a gastric pull-up procedure. The endomucosa on the esophageal side of the transection was resected and a funnel shaped UBM scaffold anastomosed proximally to the free end of the endomucosa and sutured distally through the stomach wall (see, e.g., FIGS. 4A-4C). One dog was subjected to a complete transection of the GE junction and repaired without endomucosal resection or ECM scaffold implantation. Two dogs where subjected to transaction of the GE junction followed by endomucosal resection without ECM scaffold placement.

The dogs were survived until stricture formed that prevented swallowing or elective euthanasia was performed at prescribed time points ranging from 30 to 180 days.

ECM Device Preparation

Porcine urinary bladders were harvested from market weight (approximately 110-130 kg) pigs (Whiteshire-Hamroc, Ind.). Residual external connective tissues, including adipose tissue, was trimmed and all residual urine removed by repeated washes with tap water. The urothelial layer was removed by soaking of the material in 1 N saline. The tunica serosa, tunica muscularis externa, the tunica submucosa, and most of the muscularis mucosa were mechanically delaminated from the remaining bladder tissue. The remaining basement membrane of the tunica mucosa and the subjacent tunica propria, collectively termed urinary bladder matrix (UBM), were then isolated and disinfected and decellularized by immersion in 0.1% (v/v) peracetic acid ($\sigma$), 4% (v/v) ethanol, and 96% (v/v) sterile water for 2 h. The UBM-ECM material was then washed twice for 15 min with PBS (pH=7.4) and twice for 15 min with deionized water. Multilayer tubes were created by wrapping hydrated sheets of UBM around a 22 mm perforated tube/mandrel that was covered with umbilical tape for a total of four complete revolutions (i.e., a four layer tube). To fabricate the GE junction device, a custom mold was constructed in the shape of a funnel, with a perforated straight tube (25 mm diameter) connected to a bowl (80 mm diameter). Hydrated sheets of UBM were formed around the mold until a total of four-6 layers were present. Prior to placing the ECM on the mold, the tube was wrapped with umbilical tape and the bowl was wrapped with cheese cloth to facilitate removal of the UBM. The constructs were finally placed into a plastic pouch and attached to a vacuum pump (Leybold, Export, PA, Model D4B) with a condensate trap inline. The constructs were subjected to a vacuum of 28 to 29 in Hg for 10 to 12 h to remove the water and form a tightly coupled multilayer laminate. Each device was then removed from the mandrel and terminally sterilized with ethylene oxide.

Surgical Procedures

Each animal was anesthetized by intravenous administration of sodium thiopental and a surgical plane of anesthesia was maintained by intubation and inhalation of Isofluorane in oxygen. The surgical area was shaved and prepared with standard draping for aseptic surgery.

Group 1

In this group of dogs, a midline cervical incision was made, and tissue layers dissected to isolate the esophagus. A complete transection of the esophagus was made and 1.5 cm of the endomucosa was resected from cut ends of both the proximal and distal segments. A tubular ECM scaffold was telescoped within the remaining muscularis mucosa and sutured to the proximal mucosal end with two short running sutures of either Prolene 5.0 or PDS 5.0 and to the distal end with 4 separate stitches equally spaced about the circumference. Finally an end-to-end anastomosis of the muscularis mucosa was performed with separate stitches of PDS 3.0. The cervical wound was closed by layers with Vicryl 3.0. The same procedure was repeated for the control dog without implanting the scaffold.

Group 2

In this group of dogs, a midabdominal incision was made, the triangular ligament of the liver was sectioned, and the diaphragm hiatus was dissected to expose the GE junction. A complete transverse section of the GE junction was made and 1.5 cm of the esophageal endomucosa and a 5 mm ring of gastric mucosa were resected. The funnel shaped ECM device was telescoped within the structures. The tubular segment of the device was anastomosed to the esophageal mucosa with 2 short running sutures of PDS 5.0 and the flared portion fixed to the gastric wall with 4 separate stitches of PDS 4.0. The gastroesophageal end-to-end anastomosis was completed by restoring the muscularis externa with separate 3.0 PDS sutures. The abdominal cavity was closed by layers with Vicryl 2.0, Prolene 1.0, and PDS 3.0, respectively. A chest tube was placed on the left side since the pleural cavity was opened during hiatus dissection. The same procedure was repeated for control dogs with the modifications described in the experimental design overview.

Post Surgical Care

The dogs were recovered from anesthesia, extubated and monitored in the recovery room until they were resting comfortably in sternal position. The dogs were kept in a cage overnight and returned to their larger run housing on postoperative day one. The dogs were given prophylactic antibiotics consisting of Cephalothin/Cephalexin (35 mg/kg PO), bid×7 to 9 days. After surgery the dogs received Acepromazine (0.1 mg/kg IV) and Butorphanol (0.05 mg/kg IV), followed by Buprenorphine (0.01-0.02 mg/kg, SC or IM q 12 h) thereafter for analgesia as needed. The dogs in group 2 (including controls) were given 20 mg of Omeprazole daily. Dogs were fed from an elevated/raised platform. The dog's daily nutrition was calculated and divided into 2 to 3 feedings per day. Gruel/soft food was provided for 1 week postsurgery. The animals were reintroduced to solid food over a 2 week period with oral intake starting 36 hour after surgery. The dogs were weighed weekly and housed in a run measuring approximately 10×14 ft to allow freedom to ambulate. Endoscopic examinations were completed at approximately monthly intervals to evaluate esophageal structure and function.

Morphological Examination

Immediately after euthanasia, the cervical esophagus was harvested. The harvested tissue included the scaffold placement site plus native esophageal and/or gastric tissue both proximal and distal to the graft site. The excised sample was opened by making a longitudinal incision in the distal to proximal direction. The exposed mucosal surface was examined and the tissue was then immersed in 10% neutral buffered formalin, trimmed, sectioned, and stained with both Hematoxylin and Eosin and Masson's Trichrome stains. The areas examined included the native tissue, the proximal and distal anastomoses of the scaffold, and the mid-scaffold region where the native end-to-end anastomosis was mounted.

The clinical control showed healing of the anastomosis site with scar tissue formation. There was an invagination of the mucosa and a thin band of fibrous connective tissue (scar tissue) extending from immediately beneath the mucosal epithelium to the abluminal portions of the tunica muscularis.

The experimental controls showed scarring at the anastomosis site. There was a slight invagination of the mucosal epithelial cells and a dense band of connective tissue extending from immediately beneath the mucosal epithelial cells to the outermost layer of the tunica muscularis externa.

All dogs in which the ECM biologic scaffold was placed showed an intact, confluent layer of mucosal epithelium with reconstitution of the submucosal layer and the muscularis externa layer. There were thin, scattered bands of fibrous connective tissue intermixed with islands of muscle in the region of the muscularis externa. No such new muscle tissue was seen in the dogs in which no ECM scaffold was placed.

Thus, the ECM scaffold provided constructive remodeling of all layers of the esophagus and gastroesophageal junction and minimized or prevented scar tissue formation at this site.

Having described this invention, it will be understood to those of ordinary skill in the art that the same can be performed within a wide and equivalent range of conditions, formulations and other parameters without affecting the scope of the invention or any embodiment thereof.

We claim:

1. A method of reinforcing an esophageal anastomotic site in a patient comprising implanting a tubular device comprising one or more layers of extracellular matrix either:
   in the lumen of the patient's esophagus; or
   overlaying the abluminal surface of the patient's esophagus at the anastomotic site.

2. The method of claim 1, wherein the esophageal anastomotic site is a cervical esophageal anastomotic site.

3. The method of claim 1, wherein the device has a length of between 1 to 30 cm.

4. The method of claim 1, wherein the device has a diameter of between 0.5 to 5 cm.

5. The method of claim 1, wherein the device is decellularized.

6. The method of claim 1, wherein the extracellular matrix tissue is isolated from urinary bladder tissue.

7. The method of claim 1, wherein the extracellular matrix tissue is isolated from small intestinal submucosa.

8. The method of claim 1, wherein the extracellular matrix tissue is isolated from dermis of skin.

9. The method of claim 1, wherein the extracellular matrix tissue is isolated from the esophagus.

10. The method of claim 1, wherein the device comprises 1-10 layers of extracellular matrix tissue.

11. The method of claim 1, wherein the device is seeded with cells.

12. The method of claim 1, wherein the cells are autologous.

13. The method of claim 1, wherein prior to implanting the tubular device endomucosa is removed from the lumen of the patient's esophagus, and the tubular device is implanted in the lumen and overlays at least a portion of the luminal surface from which endomucosa was removed.

14. A method of joining a resected esophagus in a patient comprising attaching a tubular device comprising one or more layers of extracellular matrix to the patient's esophagus in the lumen thereof and at the site of the resection such that the tubular device bridges the resection site.

15. The method of claim 14, wherein the resection is a cervical esophageal resection.

16. The method of claim 14, wherein the device has a diameter of between 0.5 to 5 cm.

17. The method of claim 14, wherein the device is decellularized.

18. The method of claim 14, wherein the extracellular matrix tissue is isolated from the esophagus.

19. The method of claim 14, wherein the device comprises 1-10 layers of extracellular matrix tissue.

20. The method of claim 14, wherein the device is seeded with cells.

21. The method of claim 20, wherein the cells are autologous.

* * * * *